| United States Patent [19] | [11] | 4,224,440 |
|---|---|---|
| Smith | [45] | Sep. 23, 1980 |

[54] 1-(3,5-DISUBSTITUTED-2,4,6-TRIIODO-PHENLY)-3-(POLYHYDROXY-ALKYL)UREA COMPOUNDS

[75] Inventor: Kenneth R. Smith, Black Jack, Mo.

[73] Assignee: Mallinckrodt, Inc., St. Louis, Mo.

[21] Appl. No.: 921,816

[22] Filed: Jul. 3, 1978

Related U.S. Application Data

[62] Division of Ser. No. 577,850, May 15, 1975, Pat. No. 4,109,081.

[51] Int. Cl.$^2$ ............................................. C07H 5/06
[52] U.S. Cl. ................................. 536/53; 260/553 A; 424/5; 424/180; 536/18
[58] Field of Search ................ 536/53, 18; 260/553 A

[56] References Cited

U.S. PATENT DOCUMENTS

| 2,663,729 | 12/1953 | Searle et al. | 536/53 |
| 3,158,599 | 11/1964 | Morel et al. | 536/53 |
| 4,109,081 | 8/1978 | Smith | 536/53 |

*Primary Examiner*—Johnnie R. Brown
*Attorney, Agent, or Firm*—Senniger, Powers, Leavitt and Roedel

[57] ABSTRACT

Certain 1-(3,5-disubstituted-2,4,6-triiodophenyl)-3-(polyhydroxy-alkyl)urea compounds are useful as x-ray contrast agents. Representative of this class of compounds is the compound 3-[3-(N,N-dimethylcarbamyl)-2,4,6-triiodo-5-(N-methylcarbamyl)phenyl]-1-methyl-1-(D-gluco-2,3,4,5,6-pentahydroxyhexyl)urea.

4 Claims, No Drawings

1-(3,5-DISUBSTITUTED-2,4,6-TRIIODOPHENLY)-3-(POLYHYDROXY-ALKYL)UREA COMPOUNDS

CROSS REFERENCE TO RELATED APPLICATION

This is a division of application Ser. No. 577,850, filed May 15, 1975, now U.S. Pat. No. 4,109,081.

BACKGROUND OF THE INVENTION

This invention relates to the field of organic chemistry, and more particularly to novel 1-(3,5-disubstituted-2,4,6-triiodophenyl)-3-(polyhydroxy-alkyl)urea compounds useful as non-ionic x-ray contrast media.

As is known, many 2,4,6-triiodobenzoic acid derivatives have been proposed and used as x-ray contrast agents. In general, it has been the practice to convert these compounds to salts, such as for example, the sodium and N-methylglucamine salts in order to render the compounds water-soluble and suitable for intravenous administration.

More recently, Almen et al. (U.S. Pat. No. 3,701,771, dated Oct. 31, 1972) have disclosed certain non-ionic N-(2,4,6-triiodobenzoyl)-sugar amines which ae stated to be useful as x-ray contrast agents in the cerebrospinal cavities. In these compounds, a polyhydroxyalkyl chain is coupled to an iodoaromatic moiety in order to impart water solubility without restoring to ionic species. Certain of the non-ionic compounds disclosed in this patent were reported to behighly soluble in water while others were reported to have a medium or low water solubility.

Czechoslovakian patent No. 118,444 (published May 15, 1966) discloses, as x-ray contrast media, compounds of the formula:

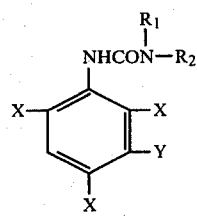

in which X is bromine or iodine and one of which may be hydrogen, Y is hydrogen, hydroxyl or methoxyl, $R_1$ is hydrogen or an alkyl with 1–4 carbon atoms and $R_2$ is carboxyalkyl with 2–6 carbon atoms, polyhydroxyalkyl with 4–6 carbon atoms or phenyl substituted in the 3- or 4- position by a carboxyl or sulfonamido group. However, it has been found that a representative compound of this class; namely, 3-[3-methoxy-2,4,6-triiodophenyl]-1-methyl-1-(D-gluco-2,3,4,5,6-pentahydroxyhexyl-)urea, is insufficiently water-soluble (i.e., less than 1% soluble) for the purpose of determining its intravenous, intracerebral or intracisternal toxicity utilizing aqueous solutions of the compound.

In certain instances, non-ionic x-ray contrast media have been found to be less toxic than their ionic counterparts. This is believed to be due at least in part to the fact that the non-ionic compounds, being substantially non-ionized in aqueous solution, create less of an osmotic imbalance than do ionic compounds, i.e., non-ionic x-ray contrast media contribute only one molecular species per iodinated moiety as compared to ionic x-ray contrast media which contribute two or more species per iodinated moiety.

An interest has developed, therefore, in the synthesis of water-soluble, non-ionic x-ray contrast media possessing low toxicity and high iodine content for use in the x-ray visualization of areas of the body such as, for example, the cardiovascular and central nervous systems where high concentrations of contrast media are required in order to provide sufficient opacity.

SUMMARY OF THE INVENTION

Among the several objects of the invention may be mentioned the provision of novel 1-(3,5-disubstituted-2,4,6-triiodophenyl)-3-(polyhydroxy-alkyl)urea compounds; the provision of such compounds which are useful for the preparation of non-ionic x-ray contrast media; the provision of certain novel intermediates which are useful in the preparation of such compounds; and the provision of methods of preparing such compounds. Other objects and features will be in part apparent and in part pointed out hereinafter.

The present invention is thus directed to compounds of the formula:

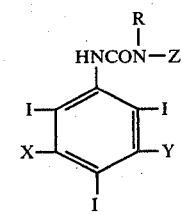

where X and Y are each non-ionizing functions compatible with low toxicity and/or water solubility in the 2,4,6-triiodophenyl configuration and

is the monovalent residue of a polyhydroxy-amine in which N is a nitrogen atom, Z is a polyhydroxylic residue, and R is selected from the group consisting of hydrogen, lower alkyl, hydroxy-lower alkyl and polyhydroxy-lower alkyl, said monovalent residue containing not more than 7 carbon atoms in its chain or ring.

The invention is further directed to intermediate compounds of the formula:

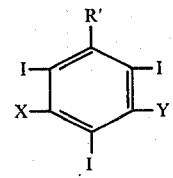

wherein X and Y are each groups which are relatively inert to isocyanate or carbamyl chloride functions and compatible with low toxicity and/or water solubility in the 2,4,6-triiodophenyl configuration or which are convertible to functions compatible with low toxicity and/or water solubility in the 2,4,6-triiodophenyl configuration and R' is selected from the group consisting of isocyanate and carbamyl chloride functions.

The invention also includes a method of preparing compounds of the formula:

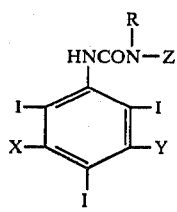

wherein X and Y are each non-ionizing functions compatible with low toxicity and/or water solubility in the 2,4,6-triiodophenyl configuration and

is monovalent residue of a polyhydroxy-amine in which N is a nitrogen atom, Z is a polyhydroxylic residue, and R is selected from the group consisting of hydrogen, lower alkyl, hydroxy-lower alkyl and polyhydroxy-lower alkyl, said monovalent residue containing not more than 7 carbon atoms in its chain or ring, which comprises reacting a compound of the formula:

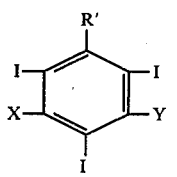

wherein X and Y are each groups which are relatively inert to isocyanate or carbamyl chloride functions and compatible with low toxicity and/or water solubility in the 2,4,6-triiodophenyl configuration or which are convertible to functions compatible with low toxicity and/or water solubility in the 2,4,6-triiodophenyl configuration and R' is selected from the group consisting of isocyanate and carbamyl chloride functions, with a polyhydroxy-amine selected from the group consisting of aldosamines N-(lower alkyl) aldosamines, ketosamines, N-(lower alkyl) ketosamines, N-(polyhydroxy-lower alkyl)amines, N-lower alkyl-N-(polyhydroxy-lower alkyl)amines, deoxyaldosamines, lower alkyl-glycosidoamines, polyhydroxy-carbocyclic amines and N-lower alkyl-(polyhydroxy-carbocyclic) amines.

DESCRIPTION OF THE PREFERRED EMBODIMENTS

In accordance with the invention, it has been found that certain novel compounds of the following structure are useful as non-ionic x-ray contrast agents:

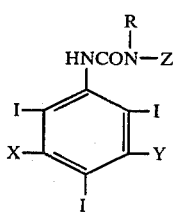

wherein X and Y are each non-ionizing functions compatible with low toxicity and/or water solubility in the 2,4,6-triiodophenyl configuration and

is the monovalent residue of a polyhydroxy-amine in which N is a nitrogen atom, Z is a polyhydroxylic residue, and R is selected from the group consisting of hydrogen, lower alkyl, hydroxy-lower alkyl and polyhydroxy-lower alkyl, said monovalent residue containing not more than 7 carbon atoms in its chain or ring.

Preferably,

is the monovalent residue of a polyhydroxy-amine from the group consisting of aldosamines, N-(lower alkyl) aldosamines ketosamines, N-(lower alkyl) ketosamines, N-(polyhydroxy-lower alkyl)amines, N-alkyl-N-(polyhydroxy-lower alkyl) amines, deoxy-aldosamines, lower alkyl-glycosidoamines, polyhydroxy-carbocyclic amines and N-lower alkyl-(polyhydroxy-carbocyclic)amines.

The aldosamines are those of the formula:

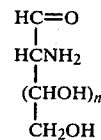

wherein n=1 to 4 and include amines such as D-erythrosamine, D-glucosamine (2-amino-2-deoxy-D-glucose), D-galactosamine and various other tetrosamines, pentosamines, hexosamines and heptosamines. Other amines of this type include 2-amino-2-deoxy-D-galactose, 2-amino-2-deoxy-D-mannose, 2-amino-2-deoxy-D-talose, 2-amino-2-deoxy-D-gulose, etc. Lower alkyl aldosamines of the formula:

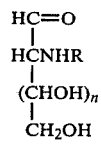

wherein n=1 to 4 and R is lower alkyl may also be employed. These amines include N-methyl-D-glucosamine (2-methylamino-2-deoxy-D-glucose), N-methyl-D-galactosamine, etc.

The ketosamines are those of the formula:

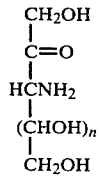

where n=1 to 3 and include amines such as D-ribulosamine, D-sorbosamine, D-fructosamine, D-gluco-heptulosamine and various other pentulosamines, hexulosamines and heptulosamines. Similarly, the N-(lower alkyl) ketosamines are those of the formula:

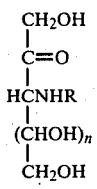

where n=1 to 3 and include amines such as N-methyl-D-sorbosamine, N-methyl-D-fructosamine, etc.

The N-(polyhydroxy-lower alkyl)amines may be of the formula:

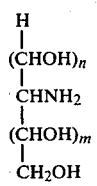

where n=0-2, m=1-5 and the sum of n+m=0-5 and include such amines as 2-amino-2-deoxy glucitol, 1-amino-1-deoxy-sorbitol, etc. and secondary amines such as diethanolamine and dipropanolamine. Other amines of this type include 1-amino-1-deoxy-D-glycero-D-guloheptitol, 1-amino-1-deoxy-D-glycero-D-galacto-heptitol, 1-amino-1-deoxy-D-glycero-1-manno-heptitol, etc.

The N-lower alkyl-N-(polyhydroxy-lower alkyl) amines include those of the formula:

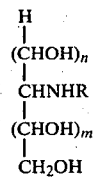

where n=0-2, m=1-5 and the sum of m+n=1-5, and R is loweralkyl and specifically include 1-deoxy-1-methylamino-sorbitol, 1-deoxy-1-ethylamino-sorbitol and 1-deoxy-1-methyl-amino-D-glucitol(N-methyl-glucamine).

Deoxy-aldosamines which may be the source of the monovalent residue of a polyhydroxy-amine include the 2-deoxy compounds of the formula:

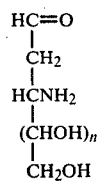

where n=1 to 3 and the corresponding 3-deoxy-aldosamines and the 4-deoxy-aldosamines.

The lower alkyl-glycosidoamines may be of the formula:

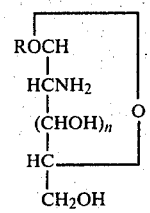

where n=1 to 3 and R is lower alkyl and include compounds such as methyl-glucosidoamine, methyl-gulosidoamine, etc.

The polyhydroxy-carbocyclic amines useful in the practice of the invention may include compounds such as 1-amino-2,3,4,5,6-pentahydroxycyclohexanes, 1-amino-2,3,4,5-tetrahydroxycyclopentanes, etc. Similarly, the lower alkyl-(polyhydroxy-carbocyclic) amines may be 1-N-methylamino-2,3,4,5,6-pentahydroxycyclohexanes, 1-N-methylamino-2,3,4,5-tetrahydroxycyclopentanes, etc.

As indicated, the monovalent residue of the polyhydroxy-amine should contain not more than 7 carbon atoms, perferably 6 or 7 carbon atoms, in its chain or cyclic ring. Further, it will be understood that primary or secondary amines of the above types may be used in the practice of the invention.

As mentioned, R may be hydrogen, lower alkyl such as methyl, ethyl or propyl, hydroxy-lower alkyl such as 2-hydroxyethyl or hydroxypropyl or polyhydroxy-lower alkyl such as dihydroxypropyl.

The substituents in the 3- and 5- positions of the ring, namely X and Y, are non-ionizing functions compatible with low toxicity and/or water solubility in the 2,4,6-triiodophenyl configuration. As is known by those skilled in the art, the term "detoxifying and/or solubilizing groups" has been used as a generic designation for a substantial number of functional groups whose occurrence in the meta-position in a 2,4,6-triiodinated moiety has come to be associated with compounds which exhibit a relatively low toxicity and/or a relatively high water solubility (cf. G. B. Hoey; P. E. Wiegert and R. D. Rands, Jr., "Organic Iodine Compounds as X-Ray Contrast Media", in *International Encyclopedia of Pharmacology and Therapeutics*, Section 76, "Radiocontrast Agents", P. K. Knoefel, Section Editor; Pergamon Press; Vol. 1, pp. 23-40, 54-73 (1971). While-the use of such terminology originated in connection with 2,4,6-triiodobenzoic acid derivatives possessing relatively low toxicity and/or relativey high water solubility, the results set forth herein are consistent with the view that substantially the same non-ionizing functions are also compatible with low toxicity and/or water solubility in the triiodinated moiety of the non-ionic compounds of the present invention.

Among the non-ionizing functions which may constitute X and Y may be mentioned the following: lower alkoxy, e.g., methoxy and ethoxy; hydroxy-(lower alkoxy), e.g., 2-hydroxy-ethoxy; lower alkoxy-(lower alkoxy), e.g., methoxy-ethoxy and ethoxy-propoxy; lower acylamino, e.g., acetamido and propionamido; lower acylamino-(lower alkyl), e.g., acetamido-methyl and acetamido-ethyl; lower acylamino-(lower acylamino), e.g., aceturamido; hydroxy-lower acylamino, e.g., hydroxy-acetamido and hydroxy-propionamido; N-(lower alkyl)-lower acylamino, e.g., N-methylacetamido and N-methyl-propionamido; N-(hydroxy lower alkyl)- lower acylamino, e.g., N-(2-hydroxyethyl) acetamido; N-(polyhydroxy lower alkyl)-lower acylamino, e.g., N-(2,3-dihydroxy propyl)acetamido; lower alkylsulfonamido, e.g., methylsulfonamido and ethylsulfonamido; N-(lower alkyl)-lower alkylsulfonamido, e.g., N-methyl-ethylsulfonamido and N-ethyl-methylsulfonamido; 3,3-bis-(lower alkyl)-ureido, e.g., 3,3-dimethylureido and 3-methyl-3-ethylureido; lower perfluoroacylamino, e.g., perfluoroacetamido and perfluoropropionamido; carbamyl; N-(lower alkyl)carbamyl, e.g., N-methylcarbamyl and N-ethylcarbamyl; N,N-di-(lower alkyl)carbamyl, e.g., N,N-dimethylcarbamyl and N,N-diethylcarbamyl; N-(hydroxy lower alkyl)carbamyl, e.g., N-(hydroxyethyl)carbamyl; N,N-di-(hydroxy lower aklyl)carbamyl, e.g., N,N-di-(hydroxyethyl) carbmyl; lower alkoxy-(lower acylamino), e.g., methoxy-acetamido and ethoxy-acetamido; lower alkoxy-alkoxy-(lower acylamino), e.g., methoxy-ethoxy-(acetamido) and ethoxy-ethoxy(acetamido); hydroxy and hydroxy-lower alkyl, e.g., hydyroxymethyl and hydroxyethyl. As used herein, the term "acyl" means RCO where R is lower alkyl and the term "lower" (e.g., lower alkyl and lower alkoxy) means that the function contains between 1 and 6 carbon atoms. Those skilled in the art will recognize that functions of the above type other than those specifically enumerated may also constitute X and Y.

In another aspect of the invention, one of X and Y may be constituted by one of the functions enumerated above and the other of X and Y may be constituted by the function

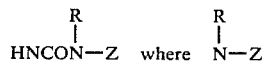
HNCON—Z where N—Z is as previously defined.

In one method aspect of the invention, the novel end products are prepared by reacting an intermediate compound of the formula:

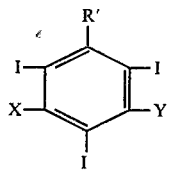

wherein X and Y are each groups which are relatively inert to isocyanate or carbamyl chloride functions and compatible with low toxicity and/or water solubility in the 2,4,6-triiodophenyl configuration or which are convertible to functions compatible with low toxicity and/or water solubility in the 2,4,6-triiodophenyl configuration and R' is an isocyanate or carbamyl chloride function with a polyhydroxy-amine of the type previously described. This reaction results in the direct prodution of the novel end products.

In the intermediate compounds of the invention, X and Y may be any of the functions previously described with the exception of those, such as amine or hydroxy, which contain hydrogen atoms reactive with the isocyanate or carbamyl chloride function. Thus, where it is desired to have X and Y in the end product be constituted by hydroxy, hydroxy-lower alkyl, hydroxy-(lower alkoxy), hydroxy-lower acylamino, N-(hydroxy lower alkyl)-lower acylamino, N-(polyhydroxy lower alkyl)-lower acylamino, N-(hydroxy lower alkyl)carba- myl and N,N-di-(hydroxy lower alkyl)carbamyl functions, they are present in the intermediate compound in a protected form, i.e., as ester, ether, acetal or ketal derivatives of such functions. The compounds resulting from the reaction of such protected intermediates with the polyhydroxyamine compound are converted into the end products of the invention by removal of the protecting groups therefrom through treatment with acid where the derivative is ether, acetal, or ketal or with base where the derivative is ester.

Exemplary of the ester protecting groups are formate, acetate, benzoate and cyclic carbonate while illustrative ether protecting groups include triphenylmethyl, methoxymethyl, benzyloxymethyl and illustrative acetal and ketal protecting groups include benzylidene, methylene, cyclohexylidene, ethylidene, isopropylidene, tetrahydropyranoxy and similar groups known to those in the art.

Alternatively, the novel end products of the invention may be prepared by either of the following reaction schemes:

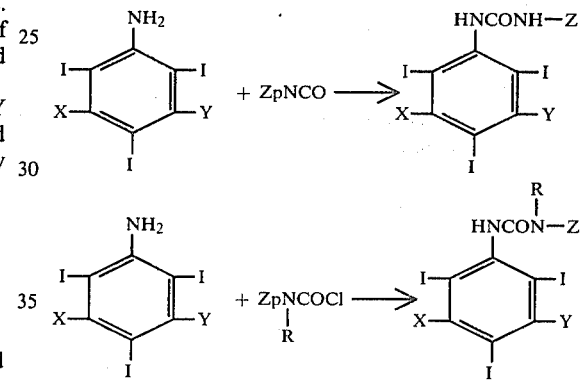

where X, Y, R and

are as previously defined and Zp represents a polyhydroxy function in protected form, i.e., with the hydroxy groups of the latter protected by being present in the form of ester, ether acetal or ketal derivatives of such groups as described above. The reactions set forth first produce intermediate compounds in which the polyhydroxy-amine function of the compounds of the invention is in protected form, these intermediates being converted into the end products of the formula shown by removal of the protecting groups as peviously described.

The novel compounds of the invention may be used as x-ray contrast agents in various radiographic procedures including those involving visualization of the central nervous system, cardiovascular visualization, myelography, ventriculography, coronary arteriography, intravenous pyelography, bronchography and urography. Certain compounds of the invention exhibit high water solubility and relatively low toxicity while other may exhibit the limited water solubility and relatively low toxicity required, for example, in oral radiographic procedures such as bronchography.

The following examples illustrate the invention.

EXAMPLE I

3-[3-(N,N-Dimethylcarbamyl)-2,4,6-triiodo-5-(N-methylcarbamyl)phenyl]-1-methyl-1-(D-gluco-2,3,4,5,6-pentahydroxyl-hexyl)urea 1. Preparation of 5-amino-2,4,6-triiodo-N-methylisophthalamyl chloride: II

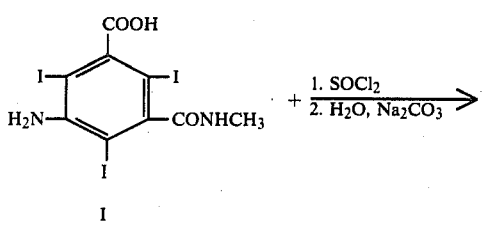

5-Amino-2,4,6-triiodo-N-methylisophthalamic acid (Hoey U.S. Pat. 3,145,197, dated Aug. 18, 1964; I; 572 g., 1 mole) was heated and stirred at reflux temperature in thionyl chloride (1.2 l.) for 4.5 hours. After concentration of the homogeneous reaction mixture under reduced pressure, the residue was dissolved in tetrahydrofuran (20 l.) and the cooled solution was extracted with a saturated aqueous solution of sodium carbonate and sodium chloride. The layers were separated and the organic layer was dried over sodium sulfate. The organic layer may be used directly to prepare 5-amino-2,4,6-triiodo-N,N,N'-trimethylisophthalamide (III) or it may be concentrated to provide the acid chloride which was pure by thin-layer chromatography (chloroform-ethyl acetate-acetic acid, 30:30:1) and whose structure was confirmed by infrared analysis.

2. Preparation of 5-amino-2,4,6-triiodo-N,N,N'-trimethylisophthalamide; III

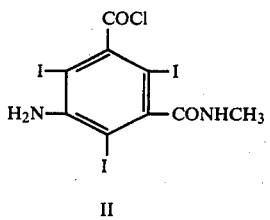

To chilled, 25% aqueous dimethylamine (1.3 l.) was added the solution of 5-amino-2,4,6-triiodo-N-methylisophthalamyl chloride (II; 1.0 mole) prepared as above in tetrahydrofuran while maintaining the solution at 20° C. After stirring overnight in an open beaker, the precipitated product (287 g. representing a yield of 48%) was collected by filtration and washed with methanol. A second crop (111 g.; 18.5%) was obtained from the mother liquor. The product (m.p. 259°–263° C. (dec.)) was pure by thin-layer chromatography (ethyl acetate-acetic acid, 98:2) and its structure was confirmed by elemental and infrared and proton magnetic resonance spectroscopic analyses.

Calc. for $C_{11}H_{12}I_3N_3O_2$: C, 22.06; H, 2.06; I, 63.56; N, 7.02. Found: C, 22.06; H, 2.17; I, 64.24; N, 6.90; C, 21.80; H, 2.06; I, 63.95; N, 6.94.

3. Preparation of 2,4,6-triiodo-5-isocyanato-N,N,N'-trimethylisophthalamide; IV

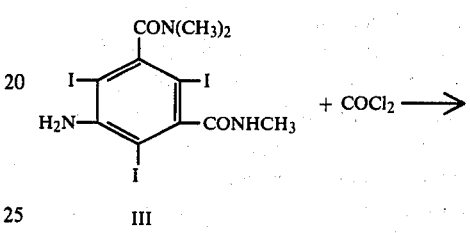

Dioxane (600 ml.) and 5-amino-2,4,6-triiodo-N,N,N'-trimethylisophthalamide (III; 119.8g., 0.2 mole) were vigorously stirred at room temperature under a nitrogen atmosphere with phosgene(160 ml.) until dissolution was effected (ca. 48 hours). The excess phosgene and solvent were removed under reduced pressure to provide the slightly impure product as a white-glassy foam in nearly quantitative yield. The structure of the product was confirmed by infrared and proton magnetic resonance spectroscopic analyses. The purity of the product could not be ascertained by thin-layer chromatography (ethyl acetate-acetic acid; 98:2) owing to hydrolysis of the isocyanate on the plate.

4. Preparation of 3-[3-N,N-dimethylcarbamyl-2,4,6-triiodo-5-(N-methylcarbamyl)phenyl]-1-methyl-1-(D-gluco-2,3,4,5,6-pentahydroxyhexyl)urea; V

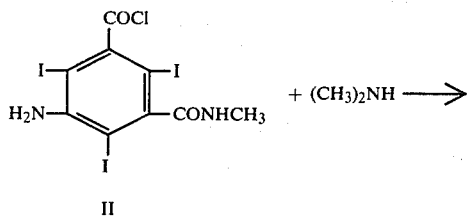

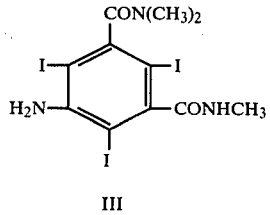

-continued

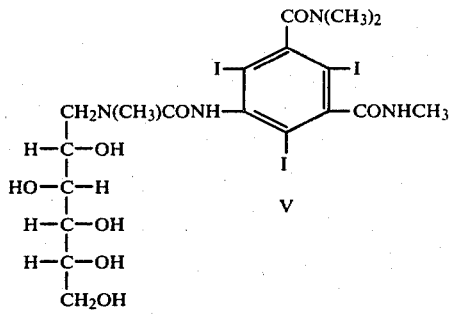

A suspension of 1-deoxy-1-methylamino-D- glucitol (29.89 g., 0.153 mole) was dissolved with heating in dimethylformamide and allowed to cool to room temperature. To this suspension was added 2,4,6-triiodo-5-isocyanato-N,N,N'-trimethylisophthalamide (IV; 23.92 g., 0.038 mole) and the reaction mixture was vigorously stirred for 3 hours at room temperature. The solvent was removed under reduced pressure (1.0 mm.) and the residue was dissolved in water (350 ml.). The aqueous solution was acidified with dilute hydrochloric acid and was repeatedly extracted with 90% phenol, and the aqueous layer was discarded. The combined phenolic extracts were washed with water (the washings were discarded) and were diluted with ether. The resulting organic layer was extracted repeatedly with water (the organic layer was discarded) and the combined aqueous layers were repeatedly washed with chloroform-isopropyl alcohol (3:1). Concentration of the aqueous layer provided 22.5 g. of product, m.p. 175°–86° C. The product was uniform by thin-layer chromatography (ethyl acetate-acetic acid-methanol, 78:2:20; ethanol-concentrated ammonium hydroxide, 1:1; and ethyl acetate-methanol-triethylamine, 32:8:2) and its structure was confirmed by infrared and proton magnetic resonance spectra and by elemental analysis. The solubility of the product in water was determined to be equal to or greater than 100% (w/v).

Calc. for $C_{18}H_{27}I_3N_4O_8$: C, 27.82; H, 3,32; I, 46.42; N, 6.83 Found: C, 27.71; H, 3.52; I, 45.83; N, 6.84.

EXAMPLE II

5-{3-[2-Gluco-2-deoxy-3,4,5,6-tetrahydroxy-1-oxo-hexyl)]ureido}-2,4,6-triiodo-N,N,N'-trimethylisophthalamide

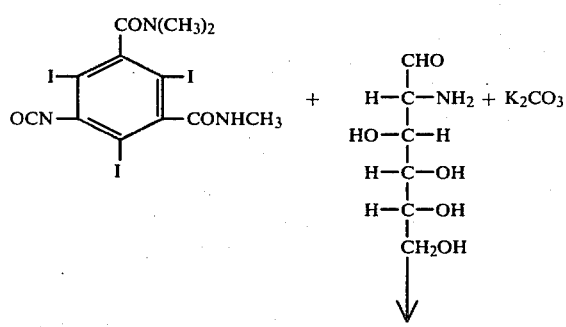

-continued

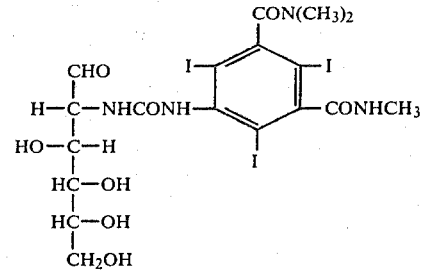

Potassium carbonate (69.11 g., 0.5 mole) and dimethylformamide (1 l.) were chilled to 0° C. under a nitrogen atmosphere and glucosamine hydrochloride (43.12 g., 0.2 mole) was added and vigorously stirred at −10° C. for one hour. 2,4,6-Triiodo-5-isocyanato-N,N,N'-trimethylisophthalamide (prepared as described in Example I3) (125 g., 0.2 mole) was added over a period of 40 minutes and the reaction mixture was vigorously stirred at −10° to 0° C. for 5 hours. After allowing the mixture to warm to room temperature overnight, the inorganic salts were removed by filtration and the solvent was removed at 35°–60° C., under reduced pressure (1.0 mm. to 0.03 mm.). The residue was stirred with water (1.2 l.) and filtered to remove a white solid. The filtrate was repeatedly extracted with 90% phenol (the aqueous layer was discarded) and the combined phenolic extracts were washed with water, discarding the washings. The washed, organic layer was diluted with ether and repeatedly extracted with water, discarding the organic layer. The combined aqueous extracts were repeatedly washed with chloroformisopropyl alcohol (3:1) and were concentrated under reduced pressure to provide the product as a white foam 36.95 g., representing a yield of 23% m.p., 193°– 198° C. (dec.). Infrared and proton magnetic resonance data were consistent with the structure assigned and the purity was shown by thin-layer chromatography (ethanol-concentrated ammonium hydroxide, 1:1 and ethyl acetate-methanol-triethylamine, 32:8:2) and by elemental analysis. The solubility of the product in water was determined to be greater than or equal to 100% (w/v).

Calc. for $C_{18}H_{22}I_3N_4O_8$: C, 26.88; H, 2.88; I, 47.35; N, 6.97.

Found: C, 26.69; H, 2.89; I, 46.98; N, 6.90, I, 47.27.

EXAMPLE III

5-{3-[2-(D-Gluco-2-deoxy-3,4,5,6-tetrahydroxy-1-oxohexyl) ]ureido}-2,4,6-triiodo-N-methyl-3-(N-methylacetamido)-benzamide 1. Preparation of 3-Amino-2,4,6-triiodo-5-(N-methylacetamide)-benzoic acid; II

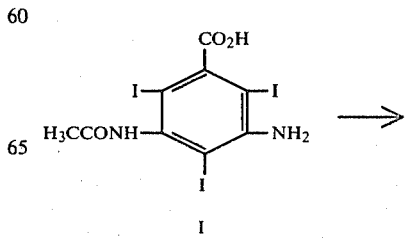

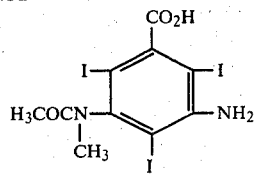

II

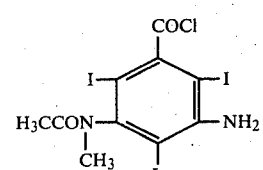

III

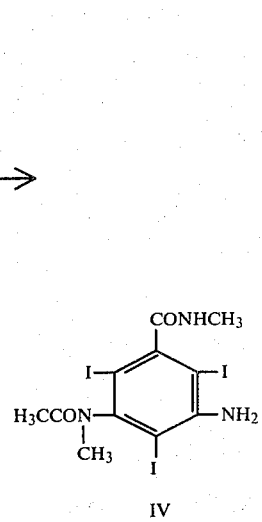

IV

3-Acetamido-5-amino-2,4,6-triiodobenzoic acid (I; 228.76 g., 0.4 mole) was added to an anhydrous ethanolic solution of sodium ethoxide (prepared from 18.4 g. (0.8 g. atom) of sodium) at 45° C. After 10 minutes, the homogeneous solution was cooled to 22° C. and methyl iodide (62.48 g.; 0.44 mole) was added. The reaction mixture was heated at 50°–55° C. for 30 minutes, at 62° C. for 30 minutes and finally at 68°–70° C. for 15 minutes. The reaction mixture was now pH 8. Methyl iodide (1 ml.) was added and heating was continued at 70° C. for 15 minutes after which the solution was neutral. The ethanol was removed under reduced pressure and water (1300 ml.) was added to the residue. The solid which dropped out of solution was collected; the filtrate was basified (~pH 10) with 50% sodium hydroxide and was washed with a 3:1 chloroform-isopropyl alcohol mixture (800 ml.). The aqueous layer was acidified to pH 5 with acetic acid and treated with activated charcoal marketed under the trade designation "Darco G-60" (5 g.) for 1 hour. The filtered solution was added to 6N hydrochloric acid (700 ml.) at room temperature to precipitate the product. The precipitate was digested for 10 minutes and was then collected, washed with water (500 ml.), and dried at 60° C. overnight to yield 193.5 g. of 3-amino-2,4,6-triiodo-5-(N-methylacetamido)-benzoic acid (82.6% yield). The product was homogeneous by thin-layer chromatography (chloroform-ethyl acetate-acetic acid, 30:20:1) and the structure of the product was confirmed by nuclear magnetic resonance spectroscopy.

2. Preparation of 3-Amino-2,4,6-triiodo-5-(N-methylacetamido)-benzoyl chloride: III

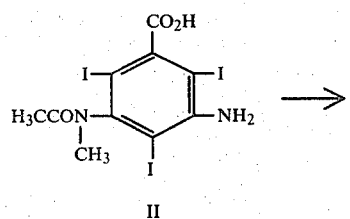

II

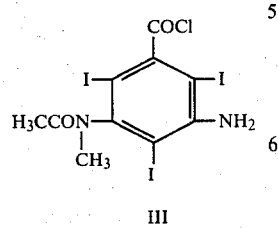

III

The procedure employed was essentially that set forth in U.S. Pat. No. 3,701,771, dated Oct. 31, 1972.

3. Preparation of 3-Amino-2,4,6-triiodo-N-methyl-5-(N-methylacetamido)-benzamide; IV 3-Amino-2,4,6-triiodo-5-(N-methylacetamido)-benzoyl chloride (III; 52.4 g.; 0.087 mole) was dissolved in tetrahydrofuran (225 ml.). The tetrahydrofuran solution was then added slowly to 40% aqueous methylamine (201.5 g.) (i.e., 80.6 g. or 2.6 moles of methylamine) at 0°–5° C. After the addition was complete, the reaction mixture was stirred at 0°–5° C. for an additional 15 minutes and then overnight at room temperature open to the air. The precipitated solid was collected, washed with water and dried at 60° C. under vacuum to give 41.75 g. (80% yield) of product. Recrystallization from methanol gave analytically pure material, m.p. 244.5°–247° C. (dec.; corr.). The product was homogeneous by thin-layer chromatography (ethyl acetate-chloroform-acetic acid, 30:20:1) and the structure of the product was confirmed by infrared and nuclear magnetic resonance spectroscopy.

Calc. for $C_{11}H_{12}I_3N_3O_2$: C, 22.06; H, 2.02; I, 63.57; N, 7.02. Found: C, 21.95; H, 2.18; I, 63.52; N, 7.17; C, 21.92; H, 2.07; I, 63.72; N, 7.20.

4. Preparation of 2,4,6-triiodo-3-isocyanato-N-methyl-5-N-methylacetamidobenzamide, V, and 3-chloro carbonylamino-2,4,6-triiodo-N-methyl-5-N-methylacetamidobenzamide, VI

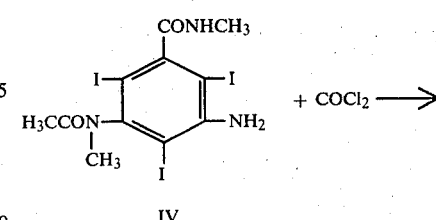

IV

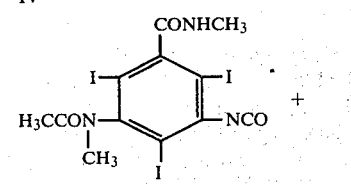

V

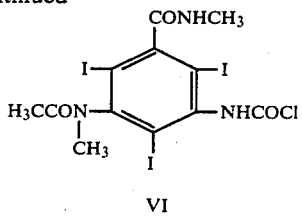

VI

Dioxane (800 ml.) and 3-amino-2,4,6-triiodo-5-(N-methylacetamido)-benzamide (IV; 119.8 g., 0.2 mole) were added to phosgene (212 ml.) and the reaction mixture stirred under a static nitrogen atmosphere for 48 hours. The excess phosgene and dioxane were removed under reduced pressure and the residue dissolved in dichloromethane (450 ml.). Anhydrous ether was added to precipitate a dark-green solid and the precipitate was removed by filtration. The filtrate was concentrated in vacuo to provide the crude isocyanate and carbamyl chloride (V and VI; 121 g., 91–97% crude yield) as shown by infrared analysis. This material is sufficiently pure for further reactions.

5. Preparation of 5-{3-[2-(D-gluco-2-deoxy-3,4,5,6-tetrahydroxy-1-oxohexy) ]ureido}-2,4,6-triiodo-N-methyl-3-(N-methylacetamido)-benzamide; VII

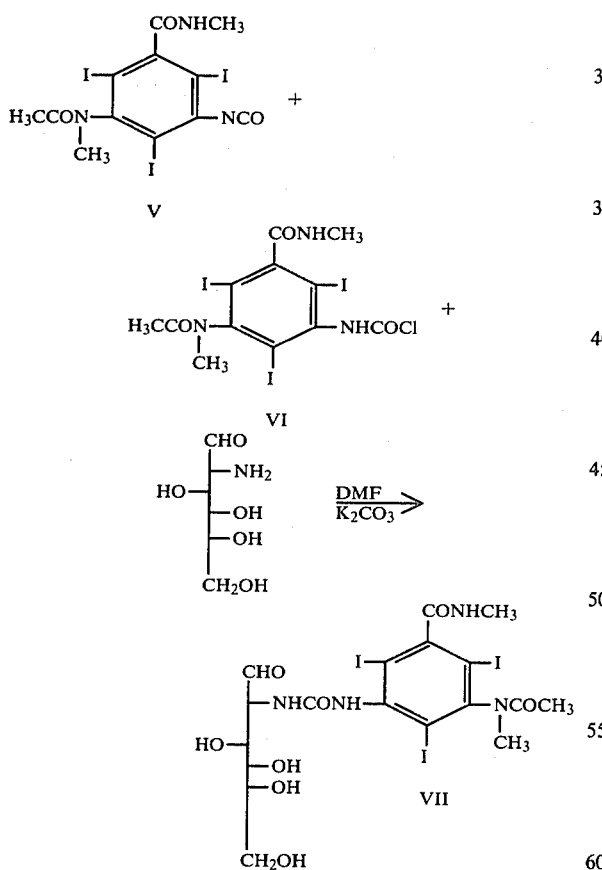

The crude isocyanate (V) which contains some of the carbamyl chloride (VI) was dissolved in dichloromethane (100 ml.) and this solution was added to a stirred slurry of glucosamine (12.30 g.) [(m.p. 115°–7° C. (un- corr.), prepared from the hydrochloride by the procedure of O. Westpahl and H. Holzmann, Chem. Ber., 75, 1274 (1942) ] and potassium carbonate (25.88 g., 0.187 mole) in dimethylformamide (312 ml.) with exothermic increase of temperature from 25° C. to 40° C. After stirring overnight, the reaction mixture was filtered and the filtrate was concentrated in vacuo (40° C., 0.1 mm.) to provide a yellow foam. The foam was slurried in water (400 ml.) for 0.5 hr. and was filtered to remove a yellow solid (discarded). The filtrate was made acidic (pH 1) with concentrated hydrochloric acid (4 ml.) and was extracted with 90% aqueous phenol (4×50 ml.) and the aqueous layer was discarded. The phenolic extracts were washed with water (4×20 ml.) and diluted with ether (750 ml.), and were extracted with water (100 ml. and 3×50 ml.). The combined aqueous extracts were extracted with chloroform-isopropyl alcohol (3:1, 6×200 ml.) and the aqueous layer was stirred overnight with decolorizing carbon (4 g.). After filtration the filtrate was concentrated in vacuo to provide 22.55 g. of desired product, m.p. 180° C. (sl. dec.), 230°–240° C. (dec.), a yield of 45%. The product was pure by thin-layer chromatography (ethanol-concentrated ammonium hydroxide, 9:1 and ethyl acetate-methanol-triethylamine, 16:4:1) and its structure was confirmed by infrared and proton magnetic resonance spectroscopy. The solubility of the product in water was determined to be greater than or equal to 100% (w/v).

Calc. for $C_{18}H_{23}I_3N_4O_8$: C, 26.88; H, 2.88; I, 47.35; N, 6.97. Found: C, 26.84; H, 3.05; I, 46.75; N, 6.85.

EXAMPLE IV

3-Acetamido-5-{3-[2-(D-gluco-2-deoxy-3,4,5,6-tetrahydroxy-1-oxohexyl]ureido}-2,4,6-triiodo-N-methylbenzamide 1. Preparation of 3-Acetamido-5-amino-2,4,6-triiodo-N-methylbenzamide; II

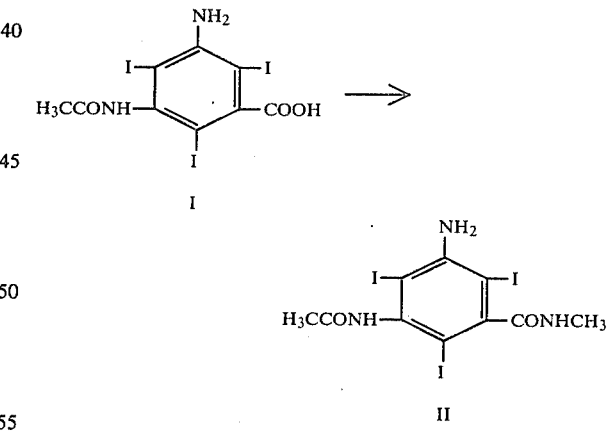

3-Acetamido-5-amino-2,4,6-triiodobenzoic acid (I; 57.2 g.; 0.1 mole) was suspended in dimethylacetamide (171 ml.). Thionyl chloride (26.1 g.; 0.22 mole) was then added slowly at 0°–10° C. After being stirred for two days at room temperature, 136.65 g. of 40% aqueous methylamine (i.e., 54.66 g. or 1.76 moles of methylamine) was added slowly at 0°–10° C. After stirring overnight at room temperature, the mixture was concentrated in vacuo. The residue was dissolved in water (500 ml.) and the mixture was stirred for three days. The precipitated solid was collected, dried and then reslurried for 1 hour in methanol (140 ml.) at reflux. After cooling overnight, the suspended solid was collected and dried, 10.66 g. (yield 18%).

Recrystallization from methanol gave analytically pure material, m.p. 210°-222° C. (dec.). The product was homogeneous by thin-layer chromatography (ethyl acetate-chloroform-acetic acid, 40:10:1) and its structure was confirmed by infrared and nuclear magnetic resonance spectroscopy.

Calc. for $C_{10}H_{10}I_3N_3O_2$: C, 20.53; H, 1.72; I, 65.09; N, 7.18. Found: C, 20.58; H, 1.93; I, 65.25; N, 7.38.

2. Preparation of 3-Acetamido-2,4,6-triiodo-5-isocyanato-N-methylbenzamide: III

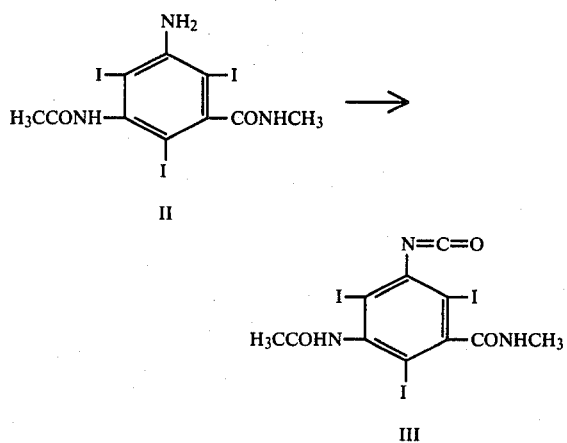

3-Acetamido-5-amino-2,4,6-triiodo-N-methylbenzamide (II; 11.7 g.; 0.02 mole) and dioxane (distilled from LiAlH$_4$; 1410 ml.) were added to redistilled phosgene (494.6 g.; 5 mole; 355.3 mol). The resulting homogeneous reaction mixture was concentrated under reduced pressure to give 13.62 g. of 3-acetamido-2,4,6-triiodo-5-isocyanato-N-methylbenzamide (III; yield greater than 100% due to carbamyl chloride being present in the 5-position as indicated by the infrared spectrum). The infrared and nuclear magnetic resonance spectra were consistent with the assigned structure.

3. Preparation of 3-acetamido-5-{3-[2-D-gluco-2-deoxy-3,4,5,6-tetrahydroxy-1-oxohexyl]ureido=-2,4,6-triiodo-N-methylbenzamide: IV

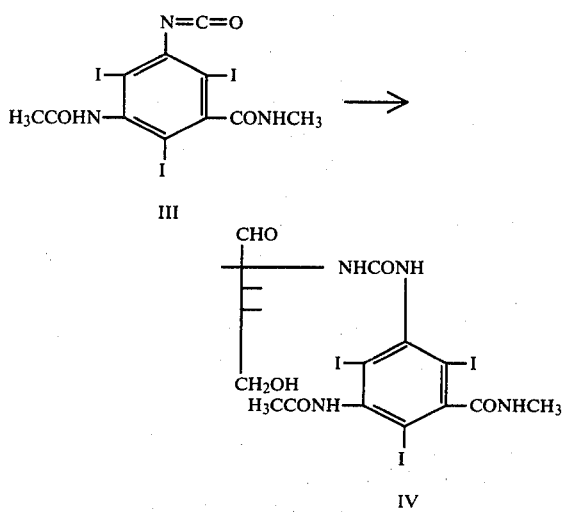

To glucosamine (1.97 g., 0.011 mole) and potassium carbonate (4.14 g.; 0.03 mole) in dimethylformamide (49 ml.) was added dropwise (required about 5 minutes) 3-acetamido-2,4,6-triiodo-5-isocyanato-N-methylbenzamide (III; 6.11 g.; 0.01 mole) dissolved in dimethylformamide (20 ml.). After being stirred overnight, the reaction mixture was filtered and concentrated in vacuo. The residue was dissolved in water (64 ml.) and the aqueous solution was adjusted to pH 1 with concentrated hydrochloric acid. The solution was extracted with aqueous 90% phenol (4×25 ml.). The combined, phenolic layers were washed with water (4×25 ml.), diluted with ether (300 ml.) and extracted with water (4×25 ml.). The combined aqueous layers were washed with chloroform-isopropyl alcohol (3:1; 5×100 ml., contact time 15 min.), treated with "Darco G-60" (0.25 g.) overnight, and evaporated under reduced pressure at 40° C. (water bath), to give 3-acetamido-5-{3-[2-D-gluco-2-deoxy-3,4,5,6-tetrahydroxy-1-oxohexyl-]ureido}-2,4,6-triiodo-N-methylbenzamide (IV) as faint-yellow foam, 5.08 g. (64.5%), m.p. 186°-251° C. (dec.). The infrared and nuclear magnetic resonance spectra were consistent with the assigned structure. The material was homogeneous by thin-layer chromatography (chloroform-methanol-triethylamine, 65:35:5) and the aqueous solubility was determined to be 18-20% (w/v).

Calc. for $C_{17}H_{21}I_3N_4O_8$: C, 25.84; H, 2.68; I, 48.19 N, 7.09. Found: C, 25.74; H, 2.93; I, 47.69; N, 7.05.

EXAMPLE V

5-{3-[2-(D-gluco-2-deoxy-3,4,5,6-tetrahydroxy-1-oxohexyl)
]ureido}-2,4,6-triiodo-N,N'-dimethylisophthalamide 1. Preparation of 5-amino-2,4,6-triiodo-N-methylisophthalamyl chloride: II

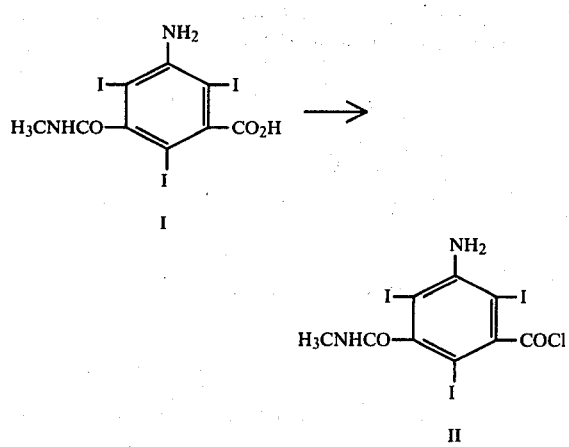

5-Amino-2,4,6-triiodo-N-methylisophthalamic acid (Hoey U.S. Pat. No. 3,145,197, dated Aug. 18, 1964; I; 571 g., 1 mole) was refluxed in thionyl chloride (600 ml.) for one hour. Additional thionyl chloride (300 ml.) was added and reflux was continued for 3.5 hours. The homogeneous reaction mixture was concentrated under reduced pressure. The residue was dissolved in tetrahydrofuran (3 l.); the solution was washed with a cold saturated solution of sodium chloride and then with cold saturated sodium chloride-sodium carbonate solution until the aqueous layer remained basic. The organic layer was dried over sodium sulfate and evaporated to one-third its original volume. The precipitated solid was collected, washed with tetrahydrofuran and dried, 235 g. (53%). The product was homogeneous by thin-layer chromatography (chloroform-ethyl) acetate-acetic acid 30:20:1) and its structure was confirmed by infrared spectroscopy.

2. Preparation of 5-amino-2,4,6-triiodo-N,N'-dimethylisophthalamide: III

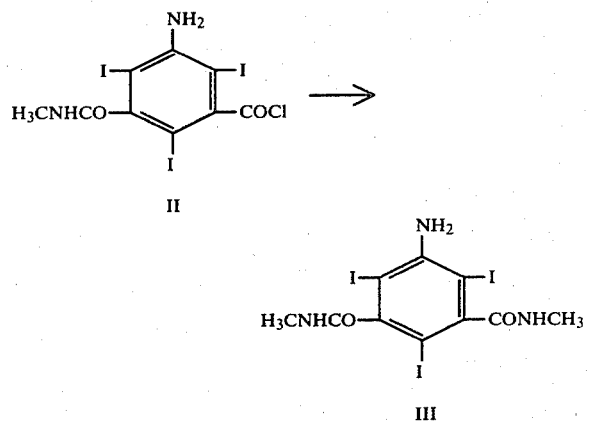

To a 0°–5° C. solution of 40% aqueous monoethylamine (560 g.; 7.2 moles) was slowly added a solution of 5-amino-2,4,6-triiodo-N-methylisophthalamyl chloride (II; 225 g., 0.38 mole) in tetrahydrofuran (1.5 l.). The resulting mixture was stirred for 2.5 hours after which the precipitated solid was collected, reslurried in dilute sodium carbonate solution and then methanol, and dried (190 g.) (85%). The product, m.p. 265°–271° C. (dec.), was homogeneous by thin-layer chromatography (ethyl acetate-acetic acid, 98:2) and its structure was confirmed by infrared spectroscopy and nuclear magnetic resonance spectroscopy.

3. Preparation of 2,4,6-triiodo-5-isocyanato-N,N'-dimethylisophthalamide: IV

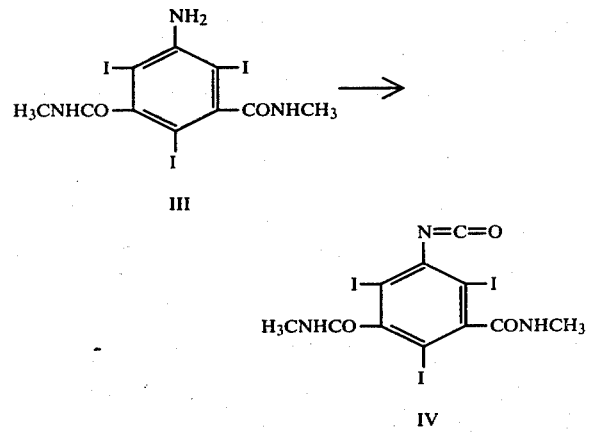

5-Amino-2,4,6-triiodo-N,N'-dimethylisophthalamide (III; 23.4 g.; 0.04 mole and dioxane (distilled from LiAlH$_4$; 2830 ml.) were added to redistilled phosgene (978.7 g.; 703 ml.; 9.89 mole). The mixture was stirred overnight at room temperature under a nitrogen atmosphere. The resulting homogeneous mixture was concentrated under reduced pressure to give 28.0 g. of 2,4,6-triiodo-5-isocyanato-N,N'-dimethylisophthalamide (IV; yield greater than 100% due to carbamyl chloride being present in the 5-position as indicated by the infrared spectrum). The infrared and nuclear magenticresonance spectra were consistent with the assigned structure.

4. Preparation of 5-{3-[2-D-gluco-2-deoxy-3,4,5,6-tetrahydroxy-1-oxohexyl)]lureido}-2,4,6-triiodo-N,N'-dimethylisophthalamide: V

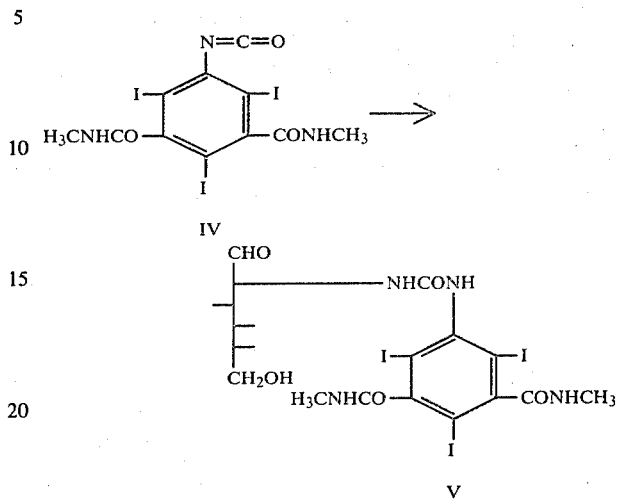

A slurry of glucosamine (0.591 g.; 0.0033 mole) and potassium carbonate (1.242 g.; 0.009 mole) in dimethylformamide (30 ml.) was heated rapidly to 75° C. (to dissolve the glucosamine) and quickly cooled in an ice bath to 25° C. 2,4,6-Triiodo-5-isocyanato-N,N'-dimethylisophthalamide (IV; 1.83 g.; 0.003 mole) dissolved in dimethylformamide (9 ml.) was added dropwise over a five minute period. After being stirred overnight at room temperature, the reaction mixture was filtered and concentrated to a foam under reduced pressure employing a 50° C. water bath. The residue was dissolved in water (24 ml.), and the aqueous solution was adjusted to pH 1 with concentrated hydrochloric acid. The solution was extracted with aqueous 90% phenol (4×10 ml.). The combined phenolic layers were washed with water (4×10 ml.), diluted with ether (120 ml.) and extracted with water (4×10 ml.). The combined aqueous extracts were washed with chloroform-isopropyl alcohol (3/1; 10×40 ml., contact time 15 min.). The aqueous solution was evaporated under reduced pressure at 40° C. (water bath) to give 5-{3-[3-D-gluco-2-deoxy-3,4,5,6-tetrahydroxy-1-oxohexyl)]ureido}-2,4,6-triiodo-N,N'-dimethylisophthalamide (V) as a colorless foam, 1.3 g. (55% yield), m.p. 175°–230° C. (dec.). The infrared and nuclear magnetic resonance spectra were consistent with the assigned structure. The material was homogeneous by thin-layer chromatography (chloroform-methanol-trimethylamine, 65:35:5; and ethanol-concentrated ammonium hydroxide, 50:50), and the aqueous solubility was determined to be 2.7–8% depending upon the method employed.

Calc. for $C_{17}H_2I_3N_4O_8$: C, 25.84; H, 2.68; I, 48.19; N, 7.09. Found: C, 26.12; H, 2.86; I, 48.28; N, 7.12.

EXAMPLE VI

3-{3-[-(D-gluco-2-deoxy-1,3,4,5,6-pentahydroxyhexyl)-]ureido}-5-[N-(2-hydroxyethyl)acetamido]-2,4,6-triiodo-N-methylbenzamide 1. Preparation of 3-acetamido-5-amino-2,4,6-triiodo-N-methylbenzamide: II

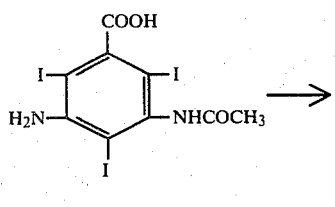

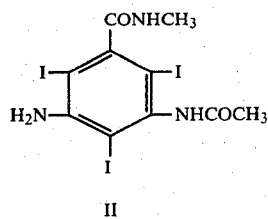

3-Acetamido-5-amino-2,4,6-triiodobenzoic acid (I; 57.2 g.; 0.1 mole) was suspended in dimethylacetamide (171 ml.). Thionyl chloride (26.1 g.; 0.22 mole) was then added slowly at 0°–10° C. After being stirred for two days at room temperature, 136.65 g. of 40% aqueous methylamine (i.e., 54.66 g. or 1.76 moles of methylamine) was added slowly at 0°–10° C. After stirring overnight at room temperature, the mixture was concentrated in vacuo. The residue was dissolved in water (500 ml.) and the mixture was stirred for three days. The precipitated solid was collected, dried and then reslurried for 1 hour in methanol (140 ml.) at reflux. After cooling overnight, the suspended solid was collected and dried, 10.66 g. (18% yield).

Recrystallization from methanol gave analytically pure material, m.p. 210°–222° C. (dec.). The material was homogeneous by thin-layer chromatography (ethyl acetate-chloroform-acetic acid, 40:10:10. The infrared and nuclear magnetic resonance spectra were consistent with the assigned structure.

Calc. for $C_{10}H_{10}I_3N_3O_2$: C, 20.53; H, 1.72; I, 65.09; N, 7.18. Found: C, 20.58; H, 1.93; I, 65.25; N, 7.38.

2. Preparation of 3-amino-5-[N-(2-hydroxyethyl)acetamido]-2,4,6-triiodo-N-methylbenzamide: III

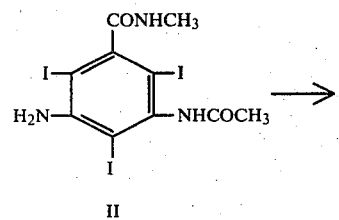

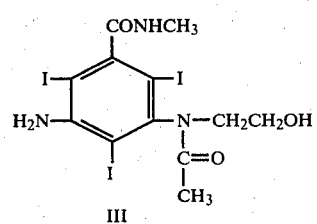

To a stirred solution of sodium ethoxide (prepared from 5.05 g. of sodium, 0.22 mole) in anhydrous ethanol (292.5 ml.) under nitrogen at 45° C. were added 3-acetamido-5-amino-2,4,6-triiodo-N-methylbenzamide, (II; 58.5 g. 0.1 mole) and dimethylformamide (60 ml.). The resulting dark green, homogeneous solution was heated at 45°–50° C. for 0.75 hr. The solution was cooled to 10° C., and 2-chloroethanol (9.65 g.; 0.12 mole) was added. The reaction mixture was then heated at 50° C. for 5 hours during which time a white precipitate formed. 2-Chloroethanol (4.025 g.; 0.05 mole) was added; the heterogeneous mixture was heated at 50° C. for 5.5 hours; 2-chloroethanol (4.025 g.; 0.05 mole) was added and the mixture was heated at 50° C. for 5 hours and then was heated at 70° C. for 3 hours. After cooling overnight, the reaction mixture was filtered. The collected solid was washed with ethanol and then slurried in 315 ml. of water for 1.5 hr. The solid was collected and dried at 75° C. resulting in 52.36 g. (83%) of 3-amino-5-[N-(2-hydroxyethyl)acetamido]-2,4,6-triiodo-N-methylbenzamide (III). The product (1 g.) was taken up in hot methanol (50 ml.). The solution was filtered and boiled down to 10 ml. The solution was stored overnight at room temperature during which time analytically pure material crystallized, 0.55 g. (55% yield for the recrystallization). The infrared and nuclear magnetic resonance spectra were consistent with the assigned structure. The material melted at 265°–267° C. (dec.); the material was homogeneous by thin-layer chromatography (ethyl acetate-acetic acid, 98:2).

Calc. for $C_{12}H_{14}I_3N_3O_3$: C, 22.91; H, 2.24; I, 60.53; N, 6.68. Found: C, 22.91; H, 2.31; I, 60.29; N, 6.57.

3. Preparation of 3-amino-2,4,6-triiodo-N-methyl-5-{N-[2-triphenylmethoxy)ethyl]acetamido}-benzamide: IV

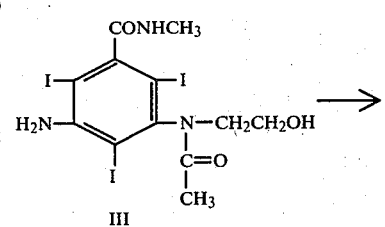

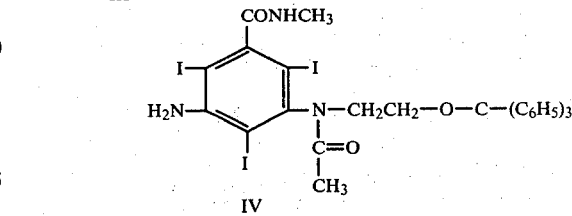

3-Amino-5-[N-(2-hydroxyethyl)acetamido]-2,4,6-triiodo-N-methylbenzamide (III; 38 g.; 0.06 mole), triphenylmethyl chloride (18.41 g.; 0.066 mole), and triethylamine (8 ml.; 5.83 g.; 0.056 mole) were slurried in N,N-dimethylacetamide (90 ml.) and heated to 90° C. to achieve solution, and the temperature was maintained at 90° C. for 6 hours. The solution was cooled to 25° C. and poured into 1 liter of stirred, distilled water and stirred 1.5 hours. The suspended solids were collected, washed with distilled water and vacuum dried to yield 68.73 g. of crude material.

This crude material was recrystallized from hot methanol (375 ml.) to yield 27.65 g. (53%). This product was single spot by thin-layer chromatography (ethyl acetate-acetic acid, 98:2). The structure of the product was confirmed by infrared and nuclear magnetic spectroscopy.

4. Preparation of 2,4,6-triiodo-3-isocyanato-N-methyl-5-{N-[2-(triphenylmethoxy)ethyl]acetamide}-benzamide: V

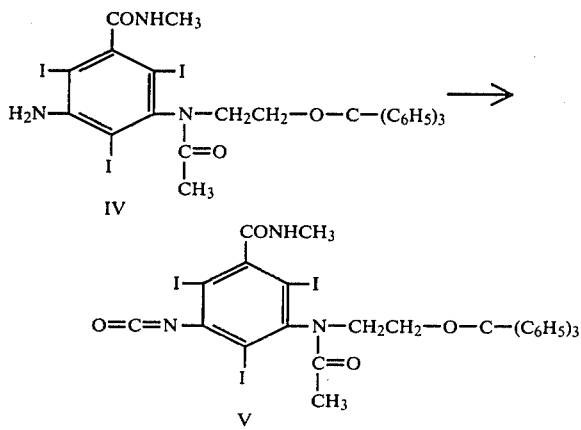

3-Amino-2,4,6-triiodo-N-methyl-5-{N-[2-(tri-phenyl-methoxy)ethyl]-acetamide}-benzamide (IV; 65.65 g.; 0.075 mole) and dioxane (distilled from LiAlH4; 525 ml.) were added to condensed phosgene (191 g.; 140 ml.; 1.92 moles). The clear, brown solution was stirred overnight at room temperature protected from moisture (drying tube). The homogeneous reaction mixture was concentrated under reduced pressure to yield 73.54 g. of 2,4,6-triiodo-3-isocyanato-N-methyl-5-{N-[2-triphenyl-methoxy)ethyl]acetamide}-benzamide (V) (>100% due to carbamyl chloride). The infrared spectrum was consistent with the assigned structure.

5. Preparation of 3-{3-[2-(D-gluco-2-deoxy-1,3,4,5,6-pentahydroxyhexyl)]ureido}-5-[N-(2-hydroxy-ethyl)acetamido]-2,4,6-triiodo-N-methylbenzamide: VI

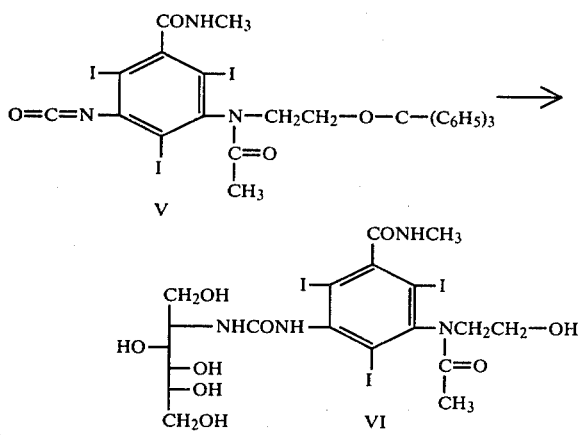

A slurry of 2-amino-2-deoxyglucitol (0.92 g.; 0.0051 mole) and potassium carbonate (1.9 g.; 0.0138 mole) in dimethylformamide (46 ml.) was heated rapidly to 75° C. (to dissolve the glucitol) and quickly cooled in an ice bath to 25° C. 2,4,6-Triiodo-3-isocyanato-N-methyl-5-{N-[2-(triphenylmethoxy)ethyl]acetamide}benzamide (V; 4.34 g.; 0.0046 mole) dissolved in dimethylformamide (14 ml.) was added dropwise over a period of 9 minutes. After being stirred overnight at room temperature, the reaction mixture was filtered and concentrated under reduced pressure. The foam-like residue was slurried in distilled water (50 ml.) overnight and filtered. The aqueous filtrate was extracted with 90% aqueous phenol (10 ml., 2×5 ml.). The combined phenolic extracts were washed with water (4×5 ml.) and diluted with ether (60 ml.). The organic layer was extracted with water (10 ml., 2×5 ml.). The combined aqueous extracts were repeatedly washed with chloroform-isopropyl alcohol (3:1). The aqueous solution was evaporated under reduced pressure at 40° C. to give 3-{3-[2-(D-gluco-2-deoxy-1,3,4,5,6-pentahydroxy-hexyl]ureido}-5-[N-(2-hydroxyethyl)acetamido]-2,3,6-triiodo-N-methylbenzamide (VI) as a pale yellow foam, 1.12 g. (23%) which was purified by column chromatography (silica gel). The infrared and nuclear magnetic resonance spectra were consistent with the assigned structure, and the water solubility was determined to be approximately 78%.

Calc. for $C_{19}H_{27}I_3N_4O_9.H_2O$:C, 26.72; H, 3.42; I, 44.57; N, 6.55. Found: C, 26.48; H, 3.38; I, 44.40; N, 6.52 44.62.

EXAMPLES VII–IX

Aqueous pharmaceutical solution formulations of the non-ionic triiodophenylureas of the invention suitable for use as x-ray contrast media in intravascular and instillation procedures may be prepared by methods familiar to those skilled in the art of formulating aqueous iodinated ionic contrast media.

Such solutions will ordinarily contain enough of the dissolved iodinated phenylurea to provide a concentration of at least approximately 14% w/v of organically bound iodine, and the solubility of many of the compounds of the invention is high enough to make possible the preparation of solutions containing as much as 50% (w/v) bound iodine, should such high concentrations be desired. In addition to the iodinated contrast agent, such solutions will ordinarily contain small concentrations of such conventional additives as a buffer, such as disodium hydrogen phosphate or sodium citrate, a chelating agent such as calcium disodium edetate, and, in some cases, an anti-oxidant such as sodium bisulfite or sodium sulfite.

As a general rule, the only additional point requiring attention in formulating the non-ionic media is the probable need for a bacteriostatic preservative that is acceptable in parenteral solutions. Most aqueous iodinated ionic contrast media are bacteriostatic as a consequence of the hypertonicity of the solution. Such inherent bacteriostaticity cannot be relied on in the case of solutions of the non-ionic agents of the invention. Such known bacteriostatic preservatives as chlorobutanol and benzyl alcohol may be used, as may other such preservatives that are acceptable for use in parenteral solutions. Exemplary formulations and their method of preparation are set forth below.

Method of Preparation

The contrast agent is dissolved in sufficient purified water for complete solution. The buffer, chelating agent, preservative and anti-oxidant are added and dissolved. Adjustments of the pH to a final value of 7.0–7.4 and of the final volume to 1,000 ml. is then accomplished by means of diluted sodium hydroxide and/or hydrochloric acid (or other suitable bases or acids) and purified water. The solution is filtered through a bacterial filter and aseptically filled into sterile containers. Alternatively, containers may be filled with the solution and thereafter sterilized. If desired, the solutions can be lyophilized.

| Type of Ingredient | Example VII | | Example VIII | | Example IX | |
|---|---|---|---|---|---|---|
| | Ingredient | Qty. | Ingredient | Qty. | Ingredient | Qty. |
| Contrast Agent | Cpd. of Ex. I | 800 g. | Cpd. of Ex. II | 1000 g. | Cpd. of Ek. III | 296 g. |
| Buffer | Sodium Citrate . 2H$_2$O | 3.0 g. | NaH$_2$PO$_4$. H$_2$O | 0.3 g. | Citric Acid | 3.0 g |
| Chelating Agent | Na$_4$EDTA | 0.1 g. | Na$_4$EDTA | 0.1 g | CaNa$_2$EDTA | 0.11 g. |
| Bacteriostatic Preservative | Chlorobutanol | 5.0 g. | Benzyl alcohol | 10 g. | Benzyl alcohol | 10.0 g. |
| Anti-Oxidant | Thiourea | 0.05 g. | Na$_2$SO$_3$ | 1.0 g. | Na$_2$SO$_3$ | 1 g. |
| Base/Acid | Dil. NaOH/HCl | qs pH 7.4 | Dil. NaOH/HCl | qs pH 7.4 | Dil. NaOH/HCl | qs pH 7.4 |
| Vehicle | Purified Water | qs 1000 ml. | Purified Water | qs 1000 ml. | Purified Water | qs 1000 ml. |
| Iodine Concentration | | 371 mg/ml. | | 474 mg/ml. | | 140 mg/ml. |

Toxicity evaluations in accordance with three different techniques were carried out on aqueous solutions of the compounds of Examples I, II and III and evaluations in accordance with two different techniques were carried out in aqueous solutions of the compounds of Examples IV and V. The techniques utilized are described below.

1. Acute Intravenous Toxicity Studies in Mice

Swiss Albino mice (Charles River) were dosed in the lateral tail vein with aqueous solutions of the above-noted iodinated compounds of Examples I, II and III having an iodine concentration of 28.2% with a pH of 7.0–7.2. The solutions were injected at the rate of approximately 1 ml./min. Following injections, the animals were observed for immediate reactions and then daily throughout a seven day observation period. The LD$_{50}$ values were calculated by the method of Litchfield and Wilcoxon (J. of Pharmac. and Exptl. Therap. 96:99-113, 1949).

2. Intracerebral Toxicity in Mice

Swiss Albino mice (Charles River) were used. Fixed volumes of aqueous solutions of the iodinated compounds were injected intracerebrally via a 27 gauge needle (¼ inch in length) according to the method of Haley et al. (Br. J. of Pharmac. 12:12-15, 1957). In the case of the compound of Example IV, a solution of the compound having an iodine concentration of 4.3% was employed and in the case of the compound of Example V, a solution of the compound having an iodine concentration of 13.3% was employed. The animals were observed immediately following injections and daily throughout a seven day observation period. The LD$_{50}$ values were calculated by the method of Litchfield and Wilcoxon (J. of Pharmac. and Exptl. Therap. 96:99-113, 1949).

3. Intracisternal Toxicity in Rats

Sprague-Dawley (Carworth) rats were used. In the case of the compound of Example IV, a solution of the compound having an iodine concentration of 7.43% was employed and in the case of the compound of Example V, a solution of the compound having an iodine concentration of 13.3% was employed. The method used was a variation of the procedure outlined by Melartin et al. (Invest. Rad. 5: 13-21, 1970). After dosing, the animals were housed individually and observed for immediate reactions and periodically for a two day observation period. The LD$_{50}$ values were calculated according to the method of Litchfield and Wilcoxon (J. of Pharmac. and Exptl. Therap. 96:99-115, 1949).

The results of these toxicity evaluations made on solutions of three compounds of the invention are set forth in Table 1.

TABLE 1
Toxicity Values of Five Compounds of the Invention

| | LD$_{50}$ Value (mg. I/kg. body wt.) | | |
|---|---|---|---|
| Compound | I.V.(Mice) | Intra-cerebral (Mice) | Intra-cisternal (Rats) |
| Example I | 1,878 | 1,500 | 21 |
| Example II | 4,817 | 1,720 | 17 |
| Example III | 6,800 | 1,460 | <40 |
| Example IV | — | >350 | 62 |
| Example V | — | >899 | >266 |

The intracerebral and intracisternal toxicity values indicate that these compounds are suitable for use as x-ray contrast agents in the visualization of the lumbar subarachnoid space.

The compounds of Examples I, II and III were employed in intravenous pyelographic studies carried out in dogs. At a dosage of 140 mg. I/kg., the compounds of Examples I and II gave good visualization of kidneys, ureters and urinary bladder five minutes after injection into dogs. At a dosage of 167 mg. I/kg., the compound of Example III gave a shadow of the kidney one minute after injection into a dog and provided better visualization of the kidneys with some visualization of the ureters five minutes after injection.

As will be apparent to those skilled in the art, other compounds within the scope of the invention in addition to those specifically disclosed in the above examples may be prepared by the same general methods.

In view of the above, it will be seen that the several objects of the invention are achieved and other advantageous results attained.

As various changes could be made in the above methods and products without departing from the scope of the invention, it is intended that all matter contained in the above description shall be interpreted as illustrative and not in a limiting sense.

What is claimed is:

1. A compound of the formula:

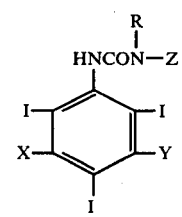

wherein X and Y are each selected from the group consisting of lower alkoxy, hydroxy-(lower alkoxy), lower alkoxy-(lower alkoxy), lower acylamino, lower acylamino-(lower alkyl), lower acylamino-(lower acylamino), hydroxy-lower acylamino, N-(lower alkyl)-lower acylamino, N-hydroxy lower alkyl) lower acylamino, N-(polyhydroxy lower alkyl) lower acylamino, lower alkylsulfonamido, N-(lower alkyl)-lower alkylsulfonamido, 3,3-bis-(lower alkyl)-ureido, lower perfluoroacylamino, carbamyl, N-(lower alkyl)-carbamyl, N-(hydroxy lower alkyl) carbamyl, N,N-di-(lower alkyl)carbamyl, N,N-di-(hydroxy lower alkyl)-carbamyl, lower alkoxy-(lower acylamino), lower alkoxy-alkoxy-(lower acylamino), hydroxy and hydroxy-lower alkyl and

is the monovalent residue of a polyhydroxy-amine selected from the group consisting of N-(lower alkyl) aldosamines, ketosamines, N-(lower alkyl) ketosamines, N-(polyhydroxy-lower alkyl) amines, N-lower alkyl-N-(polyhydroxy-lower alkyl amines, deoxyaldosamines, lower alkyl-glycosidoamines, polyhydroxycarbocyclic amines and N-lower alkyl-(polyhydroxy-carbocyclic) amines in which N is a nitrogen atom, Z is a polyhydroxylic residue, and R is selected from the group consisting of hydrogen, lower alkyl, hydroxy-lower alkyl and polyhydroxy-lower alkyl, said monovalent residue containing not more than 7 carbon atoms in its chain or ring.

2. A compound as set forth in claim 1 wherein one of X and Y is selected from the group set forth in claim 1 and the other of X and Y is

where R and

are as defined in claim 1.

3. A compound as set forth in claim 1 wherein

is the monovalent residue of a polyhydroxy-amine selected from the group consisting of ketosamines, N-(polyhydroxy-lower alkyl) amines and N-lower alkyl-N-(polyhydroxy-lower alkyl) amines.

4. A compound as set forth in claim 1 wherein X and Y are each selected from the group consisting of lower acylamino, N-(lower alkyl)-lower acylamino, N-(hydroxy lower alkyl) lower acylamino, carbamyl, N-(lower alkyl)carbamyl, N-(hydroxy lower alkyl)carbamyl and N,N-di-(lower alkyl)carbamyl.

* * * * *